United States Patent [19]
De Bliek et al.

[11] Patent Number: 6,038,467
[45] Date of Patent: Mar. 14, 2000

[54] IMAGE DISPLAY SYSTEM AND IMAGE GUIDED SURGERY SYSTEM

[75] Inventors: Hubrecht L. T. De Bliek; Frans A. Gerritsen, both of Eindhoven, Netherlands

[73] Assignee: U.S. Philips Corporation, New York, N.Y.

[21] Appl. No.: 09/008,337

[22] Filed: Jan. 16, 1998

[30] Foreign Application Priority Data

Jan. 24, 1997 [EP] European Pat. Off. ............. 97200196

[51] Int. Cl.[7] ...................................................... A61B 5/05
[52] U.S. Cl. ........................................... 600/424; 600/427
[58] Field of Search ...................... 348/51, 57; 340/727; 600/407, 424, 425, 427, 429, 428; 606/130

[56] References Cited

U.S. PATENT DOCUMENTS

| 5,134,390 | 7/1992 | Kishimoto et al. .................... 340/727 |
| 5,526,812 | 6/1996 | Dumoulin et al. ................... 128/653.1 |
| 5,742,331 | 4/1998 | Uomori et al. ............................. 348/51 |
| 5,872,590 | 2/1999 | Aritake et al. ............................. 348/57 |

OTHER PUBLICATIONS

R.A. Robb and B. Cameron, "Virtual Reality Assisted Surgery Program", Interactive Technology and the New Paradigm for Healthcare (1995) pp. 309–320.

*Primary Examiner*—William E. Kamm
*Assistant Examiner*—Ali M. Imam
*Attorney, Agent, or Firm*—Dwight H. Renfrew

[57] ABSTRACT

An image display system is provided with an image display apparatus (1) for displaying an image, the image being dependent on the position and orientation of the image display apparatus and independent of the position and posture of a user of the image display apparatus. An image guided surgery system is provided with such an image display system in order to show the user, during a medical treatment utilizing an instrument, where within the patient the instrument is situated, without the user having a direct view of said instrument.

18 Claims, 2 Drawing Sheets

IMAGE DISPLAY SYSTEM AND IMAGE GUIDED SURGERY SYSTEM

BACKGROUND OF THE INVENTION

1. Field of the Invention

The invention relates to an image display system, including an image display apparatus for displaying an image, the image being dependent on the position and/or orientation of the image display apparatus. The invention also relates to an image guided surgery system.

2. Description of Related Art

An image display system of this kind is known from the article *Virtual reality assisted surgery program* by R. A. Robb and B. Cameron in *Interactive technology and the new paradigm for healthcare* (1995) (pp. 309–320).

The user of the known image display system wears the image display apparatus on the head. The image shown to the user by the image display apparatus is dependent notably on the orientation of the head of the user. It is thus achieved that the user sees previously recorded image information while the illusion is created that the user sees said image information directly.

The cited article mentions that such an image display system can be advantageously used for medical diagnosis and surgery. In such an application the image display system shows previously recorded image information of a patient to be examined and/or treated to the user, in this case being the attending physician or surgeon, during the treatment. Such previously recorded image information includes, for example images formed by means of magnetic resonance (MRI) methods or X-ray computer tomography (CT). The user need not observe a separate monitor so as to see the previously recorded image information during the treatment of the patient, but instead of a direct view of the patient the user sees pre-recorded image information which is reproduced in conformity with the viewing direction of the user. It is a drawback of the known image display system that it is not very well possible for the user to see previously recorded image information in combination with a direct view of the patient.

SUMMARY OF THE INVENTION

It is an object of the invention to provide an image display system whereby previously recorded image information of an object can be displayed and direct observation of the object remains possible nevertheless.

This object is achieved by means of an image display system according to the invention in which the image is independent of the position and/or posture of a user of the image display apparatus.

The image display apparatus displays the previously recorded image information as an image which is dependent on the location and/or the orientation of the image display apparatus. The image information is displayed notably as an image which is dependent on the position and/or orientation of the image display apparatus relative to the object, for example reproduces a patient to be examined or treated. This image reproduces notably image information concerning the interior of the object as it would be directly visible if the object were transparent to some extent. For example, the image display apparatus displays an image of a part of the interior of the patient in the vicinity of the relevant position. The user can change the position and/or orientation in order to look past the image display apparatus so as to have a direct view of the object, without the image on the image display apparatus being changed. It is thus possible to observe the image on the display apparatus and at the same time look directly at the object or to change over quickly between observation of the image and observation of the object. Simultaneously with, or immediately before or after the observation of the image, the user can directly observe the object by looking past the image display apparatus.

A preferred embodiment of an image display system according to the invention includes a position detection system for measuring a position and/or orientation of the image display apparatus.

On the basis of the measured position and/or orientation of the image display apparatus, previously recorded image information is processed by an image processing unit of the image display system in order to derive an image therefrom which corresponds to the measured position and/or orientation of the image display apparatus. This image is displayed on the image display apparatus. Position data of a number of positions in or on the patient is recorded together with the image information. For example, fiducial markers can be used which are also recorded when the image information is recorded; however, clearly recognizable positions in the anatomy can also be used as markers. The positions of these markers are measured and the data processor derives a relation between positions in the patient and corresponding positions in the previously recorded images from the positions of said markers and the positions of the reproductions of these markers in the recorded images. The image processing unit derives an image signal from the image information on the basis of the position and/or orientation of the image display apparatus, the position of the patient and the relation between positions in the patient and in the previously recorded images, which image signal represents the image corresponding to the position of the image display apparatus relative to the patient. This image signal is applied to the image display apparatus in order to display this image. The image display apparatus can thus be used to observe image information concerning the interior of the patient in the same way as the exterior of an object can be studied by means of a magnifying glass.

A preferred embodiment of an image display system according to the invention is characterized in that the image display apparatus includes a transmission device for transmitting a position signal which represents the position and/or orientation of the image display apparatus.

The position detection system receives the position signal and derives the position of the image display apparatus therefrom. The position detection system notably derives the position of the image display apparatus relative to the patient. It is comparatively simple to measure the position of the image display apparatus because the transmission device reveals the position of the image display apparatus to the position detection system. For example, the transmission device includes some light-emitting or infrared emitting diodes (LEDs or IREDs). The position detection system comprises one or more CCD sensors and is suitable for receiving the light or infrared radiation transmitted by the transmission device. The one or more CCD sensors derive image signals from individual images from different directions of the LEDs or IREDs. The position system includes a computer for deriving the positions of the LEDs or IREDs, and hence the position of the image display apparatus, from said image signals.

A preferred embodiment of an image display system according to the invention is characterized in that the image display apparatus includes a liquid crystal display screen.

A liquid crystal display screen, i.e. a so-called LCD display, is flat. An image display apparatus including such an LCD display may have a very compact, notably flat construction. Such an image display apparatus can be readily held in the hand by the user and can hence also be easily moved across the patient by the user. Whenever the image display apparatus is placed in a new position, the image display apparatus will display image information associated with the relevant position.

The image guided surgery system according to the invention includes a position measuring system for measuring a position of an instrument and an image display system including an image display apparatus for displaying an image which represents image information and the position of the instrument the image being dependent on the position and/or orientation of the image display apparatus, but independent of the position and orientation of the head of a user viewing the image display apparatus.

The image guided surgery system shows the user, notably a surgeon, where in the operating zone the instrument is situated during the surgical treatment, for example an operation. Image information of the patient, such as CT and/or MRI images, is recorded before or during the operation. Markers provided in or on the patient are also reproduced in the images. The position measuring system measures positions of the markers in or on the patient. The position measuring system includes a computer for deriving a relation between positions in the patient and corresponding positions in the images from the positions of said markers and from the corresponding positions of reproductions of said markers in the images recorded. Using this relation, the computer also calculates the position in one or more of the recorded images which correspond to the measured position of the instrument. The image guided surgery system also includes an image processor for deriving an image signal from the recorded image information and the position of the instrument, which image signal represents a recorded image in which the position of the instrument is shown. This image is displayed by the image display apparatus. The image displayed on the image display apparatus shows the user where the instrument in the operating zone within the patient is situated, without the user having a direct view thereof. An image guided surgery system according to the invention is provided with an image display system as claimed in any one of the claims 1 to 4.

It is thus achieved that the user need not or only hardly look away to see at the same time the instrument and to see where the instrument is situated in the patient in the image on the display apparatus, and nevertheless keep a direct view of the patient or even the operating zone.

The position measuring system of the image guided surgery system is suitable for performing the functions of the position detection system of the image display system. The image processor of the image guided surgery system is suitable for performing the function of the image processing unit of the image display system.

A preferred embodiment of an image display system according to the invention is characterized in that the image display apparatus includes a holder for supporting the instrument.

Because the instrument is supported by the image display apparatus, a fixed relationship exists between the position of the instrument and the position of the image display apparatus. Using this embodiment it is achieved that the image displayed by the image display apparatus relates to a part of the patient in which the instrument is situated. Thus, the position of the instrument within the patient can be reproduced in said image. When the instrument is not (yet) in the patient, it is also possible to show on the display apparatus where the instrument will be situated in the patient when it is introduced therein via the holder. When use is made of an image display apparatus including a transmission device for transmitting a position signal which represents the position and/or orientation of the image display apparatus, the position signal also represents the position of the instrument. Consequently, it will not be necessary to measure the position of the instrument separately. For example, it is not necessary to provide the instrument with a separate transmission device, because use can be made of the transmission device of the image display apparatus.

BRIEF DESCRIPTION OF THE DRAWINGS

These and other aspects of the invention will be described in detail hereinafter on the basis of the following embodiments and with reference to the accompanying drawing; therein.

DETAILED DESCRIPTION OF THE PREFERRED EMBODIMENTS

Figure 1:
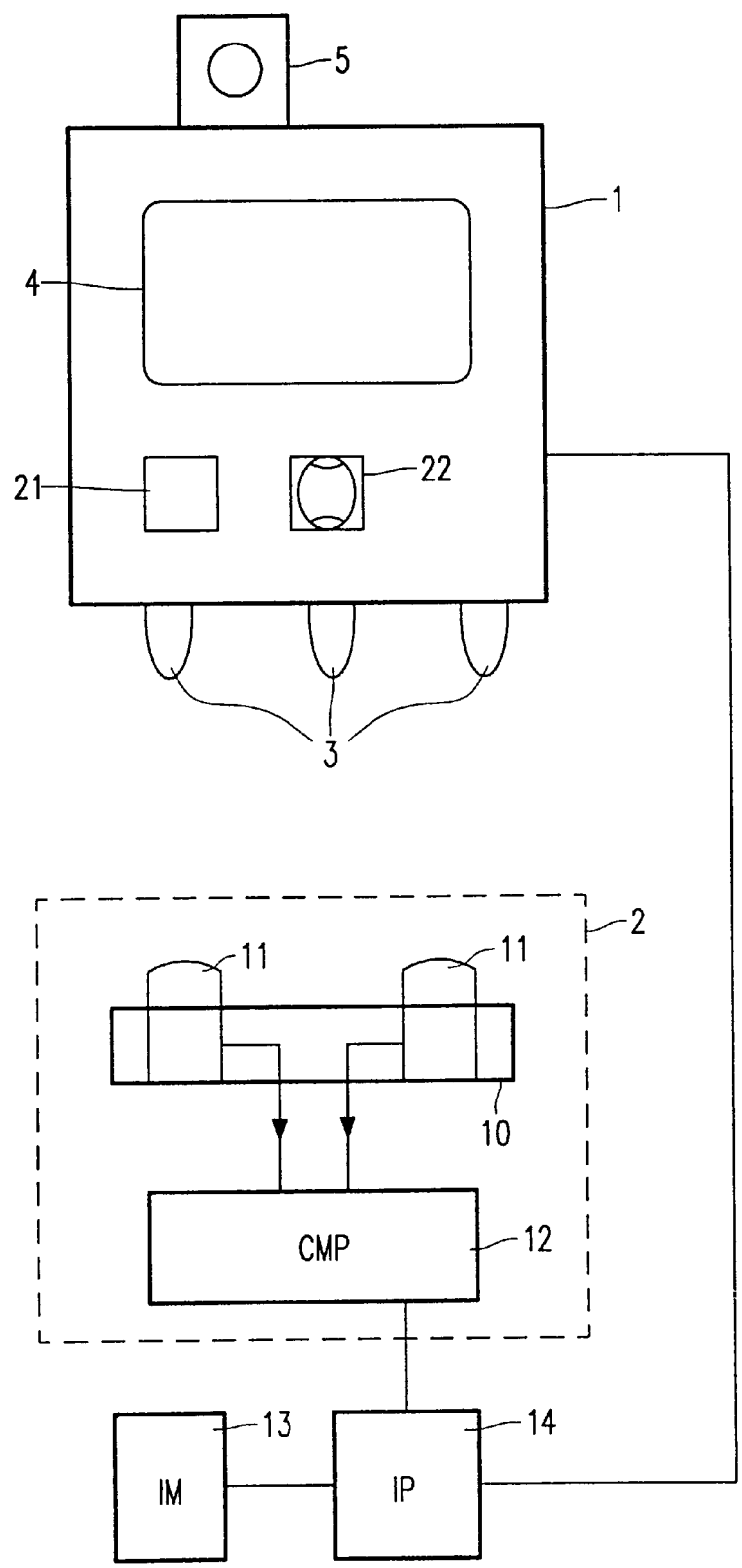
FIG. 1 shows diagrammatically an image display system according to the invention.

FIG. 1 shows diagrammatically an image display system according to the invention. The image display apparatus 1 includes an LCD screen 4 on which an image can be displayed. The image display apparatus also includes a transmission device in the form of three IREDs 3 which emit infrared radiation. The position detection system 2 includes a camera unit 10 with two infrared sensitive CCD sensors 11. Each of the CCD sensors 11 picks up images of the IREDs 3 and the image signals supplied by individual CCD sensors represent the position of the image display apparatus. Image signals of this kind are notably electronic video signals. The image signals are applied to the computer 12 which derives the position of the image display apparatus from the image signals. The computer 12 and the camera unit 10 form part of the position detection system 2. Pre-recorded image information is stored in an image memory 13. On the basis of the position of the image display apparatus 1 as derived by the computer 12, the image processing unit 14 is controlled so as to form from the image information stored an image signal which represents an image corresponding to the position of the image display apparatus 1. The computer 12 derives notably the position of the image display apparatus 1 with respect to an object being observed. The image processing unit 14 is controlled on the basis of this position in order to derive from the image information stored an image signal which represents an image in which image information of the object can be seen in the vicinity of the image display apparatus 1. It is notably possible to display image information of a part of the interior of the object in the vicinity of the image display apparatus. The image signal of the image processing unit 14 is applied to the image display apparatus 1 in order to display the image on the basis thereof. Preferably, the image signal is applied to the image display apparatus via a wireless connection, so that the image display apparatus 1 can be moved without being impeded by cables. However, it is also possible to connect the image display apparatus to the image processor by means of a cable for supplying the image signal to the image display apparatus. In that case the cable is preferably kept out of the operating zone by means of a suspension, thus ensuring that the user is not impeded by the cable.

The image display apparatus also comprises some controls, such as a push button 21 or a track ball 22, by means of which the image displayed can be adjusted or selected. Such adjustment may concern, for example zooming in or zooming out in relation to important details visible in the image, or adjustment of brightness, contrast and color of the image. The selection of the image may relate, for example to the depth within the object wherefrom image information is displayed on the image display apparatus; the user can also recall a previously displayed image. The control members may also be software implemented as so-called "icons" in the image. Such control members are activated by pointing out the relevant icon in the image by means of a cursor. It is particularly advantageous to use a pointing member, for example a pen whose position is measured by the position measuring system, in order to point out such an icon. A function indicated by the relevant icon is activated on the basis of the measured position of the pen.

Figure 2:
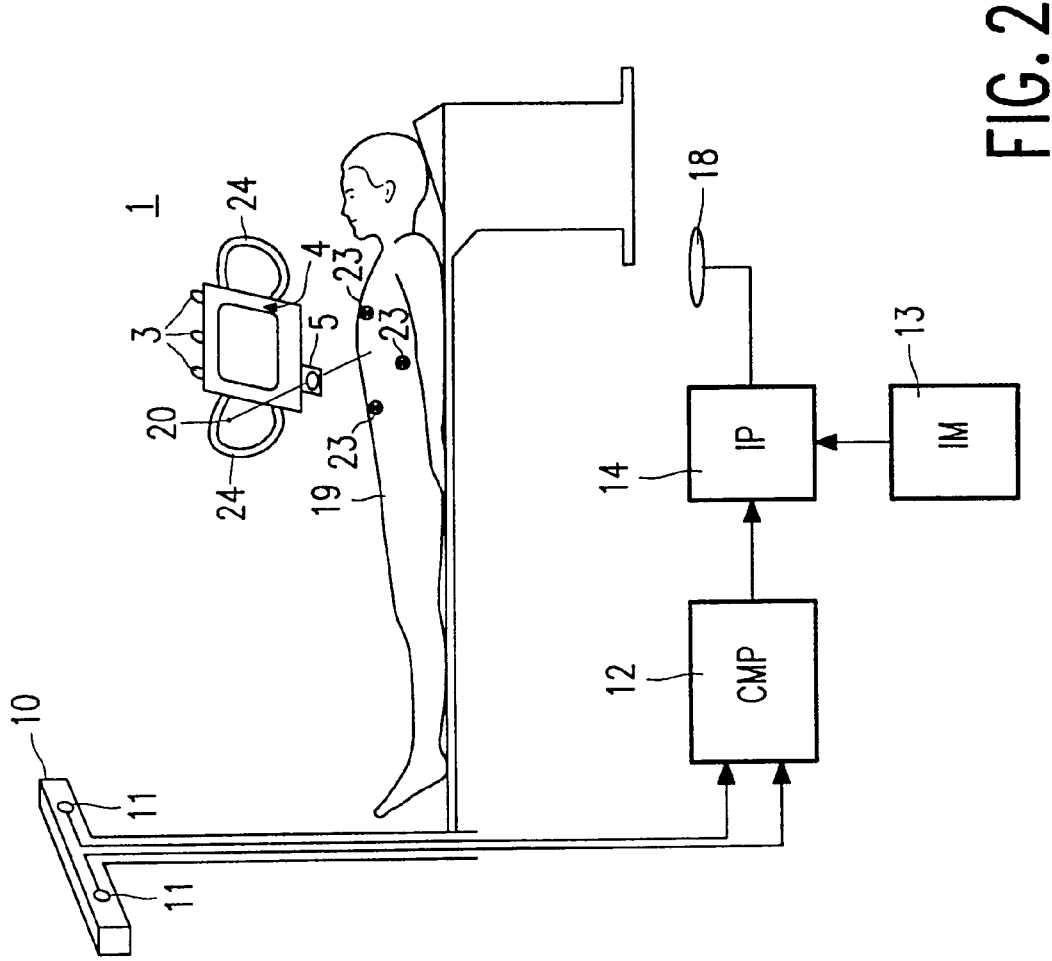
FIG. 2 shows diagrammatically an image guided surgery system in which the invention is used.

FIG. 2 shows diagrammatically an image guided surgery system in which the invention is used. The image guided surgery system includes a position measuring system which includes a camera unit 10 with two CCD image sensors 11. The camera unit picks up images of a surgical instrument 20 from different directions. The CCD image sensors supply image signals, notably electronic video signals, which represent the individual images of the instrument 20. The position measuring system also includes a computer 12 for deriving the position of the instrument 20 from the image signals. Image information of the patient 19 to be examined or treated is stored in an image memory 13. The image information comprises, for example MRI and/or CT images recorded before or during the treatment. Markers 23 on or in the patient 19 are also reproduced in the images of the patient. The position measuring system measures the positions of the markers 23, for example by pointing out the markers by means of the instrument. The computer 12 derives the relationship between positions in or on the patient 19 from the positions of the markers and the positions of the reproductions of the markers in the recorded images. On the basis of the measured position of the instrument 20 and said relationship, the image processor 14 forms an image signal which represents an image showing image information of the patient, together with the instantaneous position of the instrument 20 within the patient. The image signal is applied to the image display apparatus 1 by means of a transmitter 18. The image display apparatus then displays image information of the patient in which the position of the instrument is revealed. The user can thus move the instrument within the patient without having a direct view thereof and without risk of unnecessary damaging of tissues.

The image display apparatus includes a transmission device 3 in the form of some IREDs which emit infrared radiation. The position of the image display apparatus is measured by means of the camera unit 10 and the computer 12. On the basis of the position of the image display apparatus and the position of the instrument, the image processor forms an image signal which represents an image which shows, in dependence on the position and/or the orientation of the image display apparatus, image information of the patient together with the instantaneous position of the instrument 20 within the patient. The surgeon can thus observe the image so as to see where within the patient the instrument is situated and can at the same time keep a view of the patient and possibly also of the instrument. The image display apparatus includes a holder 5 in which the instrument 20 can be fitted. When the instrument 20 has been fitted in the holder 5, the position of the image display apparatus 1 also determines the position of the instrument 20. Thus, the image signals of the CCD image sensors 11 can be used to derive the position of the image display apparatus as well as the position of the instrument.

The image display apparatus provided with an LCD display screen 4 has a flat construction. Such an image display apparatus has a thickness of approximately 2 cm and a surface area of approximately 15 cm×20 cm. The image display apparatus also comprises grips 24, for example in the form of ears. Such an image display apparatus can be readily moved across the patient by the surgeon, notably across the operating zone, during which movement image information of the patient is continuously displayed on the display screen 4, together with the position of the instrument, as a function of the position and/or orientation of the image display apparatus relative to the patient. The surgeon can use the display apparatus as if it were a magnifying glass in order to see within the patient where the instrument is situated, without having a direct view of the instrument. The image display apparatus, however, can also be mounted on a separate stand so that the hands of the surgeon remain free to manipulate the instrument.

All references cited herein are incorporated herein by reference in their entirety and for all purposes to the same extent as if each individual publication or patent or patent application was specifically and individually indicated to be incorporated by reference in its entirety for all purposes.

We claim:

1. An image display system comprising:
    an image display apparatus for displaying a derived image of an object, the image display apparatus being positioned adjacent to the object and being moveable with respect to the object, and
    an image processing unit for processing previously-recorded image information of the object into the derived image, wherein the derived image corresponds to an instantaneous position and/or orientation of the image display apparatus relative to the object but is independent of the instantaneous position and orientation of a head of a user viewing the image display apparatus,
    whereby the user can move to view the adjacent object without the derived image displayed on the image display apparatus being changed.

2. An image display system as claimed in claim 1, further comprising a position detection system for measuring a position and/or orientation of the image display apparatus relative to the object.

3. An image display system as claimed in claim 2, wherein the image display apparatus includes a transmission device for transmitting a position signal which represents the position and/or orientation of the image display apparatus.

4. An image display system as claimed in claim 1, wherein the image display apparatus includes a liquid crystal display screen.

5. The system of claim 1 wherein the previously-recorded image information concerns the interior of the object.

6. The system of claim 1 wherein the image display apparatus further comprises controls for adjusting or selecting the display of the derived image.

7. An image-guided surgery system comprising:
    an image display apparatus for displaying a derived image of an patient, the image display apparatus being positioned adjacent to the patient and being moveable with respect to the patient, a position measuring system for measuring a position of an instrument and a position of the moveable image display apparatus, and an image processing unit for processing previously-recorded image information of the patient into the derived image, wherein the derived image represents the measured position of the instrument in an operating zone of the patient and corresponds to the measured position and/or orientation of the image display apparatus relative to the patient but is independent of the position and orientation of a head of a user viewing the image display apparatus, whereby the user can move to view the operating zone of the adjacent patient without the derived image displayed on the image display apparatus being changed.

8. An image-guided surgery system as claimed in claim 7, wherein the image display apparatus includes a holder for supporting the instrument.

9. An image display system as claimed in claim 2, wherein the image display apparatus includes a liquid crystal display screen.

10. An image display system as claimed in claim 3, wherein the image display apparatus includes a liquid crystal display screen.

11. An image display system as claimed in claim 7, which also includes a position detection system for measuring a position and/or orientation of the image display apparatus.

12. An image display system as claimed in claim 7, wherein the image display apparatus includes a transmission device for transmitting a position signal which represents the position and/or orientation of the image display apparatus.

13. An image display system as claimed in claim 11, wherein the image display apparatus includes a liquid crystal display screen.

14. An image display system as claimed in claim 12, wherein the image display apparatus includes a liquid crystal display screen.

15. The system of claim 7 wherein the image display apparatus further comprises a liquid crystal display screen.

16. The system of claim 7 wherein the image display apparatus further comprises grips for ready movement by the user of the image display apparatus relative to the patient.

17. The system of claim 7 wherein the previously-recorded image information concerns the interior of the patient.

18. The system of claim 17 wherein the previously-recorded image information is recorded by means of magnetic resonance or computed tomographic imaging of the patient.

* * * * *